US005915377A

United States Patent [19]

Coffee

[11] Patent Number: 5,915,377

[45] Date of Patent: Jun. 29, 1999

[54] DISPENSING DEVICE PRODUCING MULTIPLE COMMINUTIONS OF OPPOSING POLARITIES

[75] Inventor: Ronald Alan Coffee, Haslemere, United Kingdom

[73] Assignee: Electrosols, Ltd., Surrey, United Kingdom

[21] Appl. No.: 08/750,492

[22] PCT Filed: May 25, 1995

[86] PCT No.: PCT/EP95/02001

§ 371 Date: Jan. 24, 1997

§ 102(e) Date: Jan. 24, 1997

[87] PCT Pub. No.: WO95/32807

PCT Pub. Date: Dec. 7, 1995

[30] Foreign Application Priority Data

May 27, 1994 [GB] United Kingdom .................... 9410658

[51] Int. Cl.$^6$ .................................................... A61M 11/00

[52] U.S. Cl. ................................ 128/200.16; 128/200.14; 128/203.12; 239/690; 239/171; 239/172; 239/691; 239/695

[58] Field of Search ......................... 128/200.14, 200.16, 128/203.12; 239/690, 690.1, 696, 706, 708, 691, 695, 171, 172; 361/226–229

[56] References Cited

U.S. PATENT DOCUMENTS

| | | | |
|---|---|---|---|
| 2,723,646 | 11/1955 | Ransburg . | |
| 2,945,443 | 7/1960 | Auer et al. . | |
| 3,096,762 | 7/1963 | Winchell | 128/190 |
| 3,131,131 | 4/1964 | Wehner . | |
| 3,232,292 | 2/1966 | Schaefer | 128/172 |
| 3,296,491 | 1/1967 | Brown | 239/15 |
| 3,456,646 | 7/1969 | Phillips et al. | 128/173 |
| 3,654,501 | 4/1972 | Secker | 310/10 |
| 3,837,573 | 9/1974 | Wagner | 239/15 |
| 3,897,905 | 8/1975 | Tadewald | 239/15 |
| 3,930,061 | 12/1975 | Scharfenberger | 427/27 |
| 3,958,959 | 5/1976 | Cohen et al. | 55/10 |
| 4,073,002 | 2/1978 | Sickles et al. | 361/227 |
| 4,150,644 | 4/1979 | Masaki et al. | 123/119 |
| 4,186,886 | 2/1980 | Sickles | 239/691 |
| 4,198,781 | 4/1980 | Dykes . | |
| 4,203,398 | 5/1980 | Maruoka | 123/119 |
| 4,266,721 | 5/1981 | Sickles | 239/3 |
| 4,356,528 | 10/1982 | Coffee | 361/226 |
| 4,380,786 | 4/1983 | Kelly | 239/690 |
| 4,439,980 | 4/1984 | Biblarz et al. | 60/39.06 |
| 4,467,961 | 8/1984 | Coffee et al. | 239/1 |

(List continued on next page.)

FOREIGN PATENT DOCUMENTS

| | | |
|---|---|---|
| 0 120 633 A2 | 10/1984 | European Pat. Off. . |
| 0 102 713 B1 | 9/1987 | European Pat. Off. . |
| 0 243 031 A1 | 10/1987 | European Pat. Off. . |
| 195704 | 12/1980 | New Zealand . |
| 198774 | 10/1981 | New Zealand . |
| 191545 | 6/1984 | New Zealand . |
| 2 128 900 | 5/1984 | United Kingdom . |
| 2 201 873 | 9/1988 | United Kingdom . |
| WO 94/12285 | 6/1994 | WIPO . |
| WO/94/19042 | 9/1994 | WIPO . |

OTHER PUBLICATIONS

Article entitled: Electro–osmosis Controls Fluid in Novel Transducer Concept by Product Engineering, dated Jul. 4, 1970 authored by: Ray Lewis, Cleveland; pp. 71–72.

Article entitled: Electrodynamic Crop Spraying, dated 1981; authored by: R. A. Coffee; Reprinted from Outlook on Agriculture vol. 10, No. 7, 1981; includes excerpt pp. 350–356.

*Primary Examiner*—Kimberly L. Asher
*Attorney, Agent, or Firm*—Cobrin & Gittes

[57] ABSTRACT

A device for comminuting a liquid, which produces at least two sprays of droplets formed by electrohydrodynamic comminution, the device being arranged so that in use sprays of opposing polarity are formed which are substantially admixed after formation, so as to provide a comminution having a residual electrical charge.

13 Claims, 4 Drawing Sheets

U.S. PATENT DOCUMENTS

| | | | |
|---|---|---|---|
| 4,476,515 | 10/1984 | Coffee | 361/226 |
| 4,508,265 | 4/1985 | Jido | 239/3 |
| 4,509,694 | 4/1985 | Inculet et al. | 239/697 |
| 4,549,243 | 10/1985 | Owen et al. | 361/228 |
| 4,630,169 | 12/1986 | Kelly | 361/225 |
| 4,659,012 | 4/1987 | Coffee | 239/3 |
| 4,671,269 | 6/1987 | Wilp | 128/202.25 |
| 4,703,891 | 11/1987 | Jackson et al. . | |
| 4,735,364 | 4/1988 | Marchant | 239/690.1 |
| 4,748,043 | 5/1988 | Seaver et al. | 427/30 |
| 4,749,125 | 6/1988 | Escallon et al. | 239/3 |
| 4,776,515 | 10/1988 | Michalchik | 239/3 |
| 4,788,016 | 11/1988 | Colclough et al. | 264/10 |
| 4,801,086 | 1/1989 | Noakes | 239/3 |
| 4,830,872 | 5/1989 | Grenfell . | |
| 4,846,407 | 7/1989 | Coffee et al. | 239/690 |
| 4,962,885 | 10/1990 | Coffee | 239/3 |
| 4,979,680 | 12/1990 | Bauch et al. | 239/692 |
| 5,044,564 | 9/1991 | Sickles | 239/690.1 |
| 5,086,972 | 2/1992 | Chang et al. | 239/3 |
| 5,118,942 | 6/1992 | Hamade | 361/225 |
| 5,180,288 | 1/1993 | Richter et al. . | |
| 5,222,663 | 6/1993 | Noakes et al. | 239/3 |
| 5,267,555 | 12/1993 | Pajalich | 128/200.14 |
| 5,378,957 | 1/1995 | Kelly | 361/227 |
| 5,381,789 | 1/1995 | Marquardt | 128/202.25 |
| 5,402,945 | 4/1995 | Swanson, Jr. . | |
| 5,409,162 | 4/1995 | Sickles | 239/3 |
| 5,483,953 | 1/1996 | Cooper | 128/200.22 |
| 5,511,726 | 4/1996 | Greenspan et al. | 239/102.2 |
| 5,655,517 | 8/1997 | Coffee . | |

DISPENSING DEVICE PRODUCING MULTIPLE COMMINUTIONS OF OPPOSING POLARITIES

TECHNICAL FIELD

The invention relates to a dispensing device for comminuting a liquid and the use of such a device, in particular, in medicine.

BACKGROUND TO THE INVENTION

Known nasal sprays generally produce droplet-sprays by mechanical means. The sprays so produced contain droplets within a broad range of droplet diameters which significantly reduces targeting accuracy and hence accuracy of dosing. The non-uniform nature of the sprays can also be very wasteful of medicament.

Dispensing devices are known which produce a finely divided spray of liquid droplets by electrostatic (more properly referred to as 'electrohydrodynamic') means. The droplet spray in such devices is generated by applying an electric field to a liquid at a spray head or spray edge. The potential of the electric field is sufficiently high to provide comminution of the liquid from the spray head. The droplets produced are electrically charged and thus are prevented from coagulating by mutual repulsion.

We have now discovered that electrohydrodynamic spray technology may be used to deliver charged monodisperse liquid droplets sprays, especially medicament sprays, to the upper respiratory tract and especially to the nasal mucosa, in an efficient and very controllable manner.

We have also discovered that for optimum targeting of the spray in the upper respiratory tract it is desirable to partially remove the electric charge from the droplet sprays produced by electrohydrodynamic comminution devices. To date the principal method used to effect charge removal has required the use of a discharging electrode having a sharp or pointed edge and located downstream from the spray head. This discharging electrode produces a cloud of charged ions from the surrounding air having an opposite electrical charge of equal magnitude to that on the comminuted liquid spray. In use, the ion cloud is attracted towards, collides with and thereby electrically discharges or partially discharges the liquid spray.

European Patent number 0234842 discloses an electrohydrodynamic inhaler wherein the spray of charged droplets is discharged by means of such a discharge electrode. The droplets are discharged in order to facilitate droplet deposition into the respiratory tract as otherwise the electrically charged droplets would deposit onto the mouth and throat of the user.

A particular problem associated with the use of the sharp discharge electrode is that the highly mobile ion cloud from the discharge electrode often interferes with the comminution of the liquid spray. The inhaler device of EP 0234842 attempts to ameliorate the effects of the ion cloud at the spray head by using a neutral shield electrode located close to the spray head. In addition, the level of control over the partial discharging of the liquid spray, especially the uniformity of charge across the spray cloud, tends to vary within wide limits between zero and the original maximum.

SUMMARY OF THE INVENTION

The present invention provides a device which enables the charged spray to be partially discharged in a well controlled manner without affecting the efficiency of the comminution of the liquid spray.

Accordingly, there is provided a device for comminuting a liquid for dispensing to the upper respiratory tract, which comprises at least two electrohydrodynamic comminution means arranged so that in use comminutions of opposing polarity are formed which are substantially admixed after formation, so as to provide a comminution having a residual electrical change.

The electrohydrodynamic comminution means may be any conventional electrohydrodynamic comminution means, for example those described in the above mentioned patent specifications.

Suitably, each comminution means comprises a comminution site, generally being a surface or edge, from which the liquid comminution is produced.

A preferred comminution surface or edge is provided by a thin capillary tube, a nozzle or a slot defined by two parallel plates. However any comminution surface or edge described in the above mentioned patent specifications may be used suitably adapted for administration to the upper respiratory tract.

The device generally comprises an even number of comminution means but this is not essential, the key factors are that at least two of the comminution means provide comminutions of opposing polarity and that the comminutions produces are arranged to substantially admix.

Suitably, the device comprises 2, 4 or 6 comminution means, however higher numbers can be used as required. An example of a device is that which has 2 comminution means. An example of a device is that which has 6 comminution means.

Suitably, each comminution means comprises a means for supplying liquid to the comminution site.

Appropriate means for supplying liquid to the comminution site include mechanical, electrical or electronic powered means such as pumps which are capable of providing the required flow rate of liquid to the comminution site.

The comminution means of the invention can be used with a large range of flow rates, but generally operates with flow rates in the range of between 0.1 to 500 $\mu$L per second, such as 0.5 to 5 $\mu$L per second, especially for inhaled administration, or 10 to 200 $\mu$L per second.

A suitable means for supplying the liquid includes a syringe pump or an electrically powered pump as described in EP 0029301.

It will be appreciated from the foregoing that the comminution means generally comprises a comminution site, a means for supplying a liquid to the comminution site and a means for electrically charging the comminution site to an electric potential sufficient to comminute the liquid in use.

Accordingly, in one particular aspect of the invention there is provided a device for comminuting a liquid for dispensing to the upper respiratory tract, which comprises at least two electrohydrodynamic comminution means each comprising a comminution site, a means for supplying a liquid to the comminution site and a means for electrically charging the comminution site to an electric potential sufficient to comminute the liquid in use, wherein the comminution means are arranged so that in use comminutions of opposing polarity are formed which are then substantially admixed so as to provide a comminution having a residual electrical change.

Suitably, each comminution means comprises a means for electrically charging the said comminution site to a potential sufficient to provide comminution of the liquid, the potential usually being of the order of 1–20 kilovolts.

The means for electrically charging the said comminution site, such as a surface or edge, may be provided by any conventional high voltage generator having the appropriate output, one particularly convenient generator being a piezo-electric generator.

The piezoelectric material for the generator may be chosen from several types, such as barium titanate ceramic, or pvdf polymers, which generate significant high-voltage electric charge displacement upon being pressurized. The choice and capacity may be so chosen as to offer control of the degree of pumping and/or atomization when operated.

The required voltage for use is provided when the piezo-electric generators are squeezed, and again (with opposite polarity) when the piezo-electric generators are released from pressure.

The residual electrical change on the admixed comminution may be positive or negative charge and of course is less than the positive or negative charge on any of the premixed comminutions. The residual charge on the admixed comminution is arranged so as to optimise targeting of the comminution to the upper respiratory tract.

The residual charge on the admixed comminution may be fixed for any given device or the arrangement may be such that the net residual charge on the admixed comminution may be regulated in a controlled manner. Thus the device of the invention optionally comprises a means for regulating the electrical charge on a comminution produced from any of the comminution means prior to admixture.

Suitable means for regulating the electrical charge on a comminution may be provided by a variety of methods, such as by incorporating a means for regulating the charging means so as to provide variable voltage output and/or a means for regulating the means for supplying a liquid to the comminution site so as to vary the liquid flow rate to the comminution site.

Suitable arrangements of the comminution means which enable the comminutions produced to be admixed includes any arrangement wherein the comminution means are relatively located so as to enable the comminutions to substantially admix. Favourably, the comminution means are arranged so that the comminutions produced are directed to converge into a mixing zone. For example, when the device comprises two comminution means they may be angled towards each other so as to produce comminutions which converge into the mixing zone. Or when the device comprises three or more comminution means, they may be arranged so that the comminutions are directed to converge radially into the mixing zone. Alternatively, the relative location of the comminution means may be arranged such that the mutual attraction of the comminutions produced is sufficient to allow substantial admixing, for example they may be in a mutually parallel manner.

It is envisaged that a liquid supply means may supply one or more of the comminution means of the invention.

Alternatively, a liquid supply means may supply only one comminution means.

From the foregoing it will be appreciated that it is an aspect of the present invention that comminuted sprays from different liquids may be mixed as required. Such liquids may be capable of providing a new product on admixture or they may comprise components which are so capable. The device may also be used to mix two liquids which are reactive components of a rapid chemical reaction. In each case the mixed droplets may then be applied as a spray, with a charge-to-mass ratio on the droplets that will be the residual after the two opposing charges have been used to coalesce the liquids.

Similarly, the present device may be used to mix components which are incompatible one with the other and which therefore are advantageously admixed at the point of use.

The comminution means of the dispenser is arranged to provide liquid droplets within a diameter range compatible with targeting to the upper respiratory tract, generally being within the range of from 10 to 500 microns in diameter, such as 10 to 200 microns and especially 10 to 25 microns in diameter.

For a given liquid the diameter of the droplets can be controlled by varying the applied voltage and liquid flow rate using routing experimental procedures. Liquids having viscosities within the range of from 1 to 500 centipoise and resistivities in the range of from $10^2$–$10^8$ ohm m can be comminuted by the present device.

Medicaments suitable for delivery by the device include those used for the treatment of disorders of the upper respiratory tract including disorders of the nasal mucosa, in particular congestion and disorders of the upper respiratory tract associated with hay fever. Medicaments suitable for delivery by the device also include those used for the treatment of sore throat.

Particular medicaments include nasal decongestants such as oxymetazoline, xylometazoline, phenylephrine, propylhexadrine, nephazoline and tetrahydrozoline and as appropriate salts thereof such as the hydrochloride salt, and formulations thereof.

When used herein 'a comminution' includes a liquid droplet spray.

When used herein 'medicament' includes proprietary medicines, pharmaceutical medicines and veterinary medicines.

When used herein, unless more specifically defined herein, administration to the upper respiratory tract includes in particular the nasal mucosa.

The liquid medicinal formulations for use in the device of the invention may be formulated according to conventional procedures, such as those disclosed in the US Pharmacopoeia, the European Pharmacopoeia, 2nd Edition, Martindale The Extra Pharmacopoeia, 29th Edition, Pharmaceutical Press and the Veterinary Pharmacopoeia.

The invention may now be described, by way of example, with reference to the accompanying drawings.

DETAILED DESCRIPTION OF PREFERRED EMBODIMENTS

Comminution Sites

Figure 1:
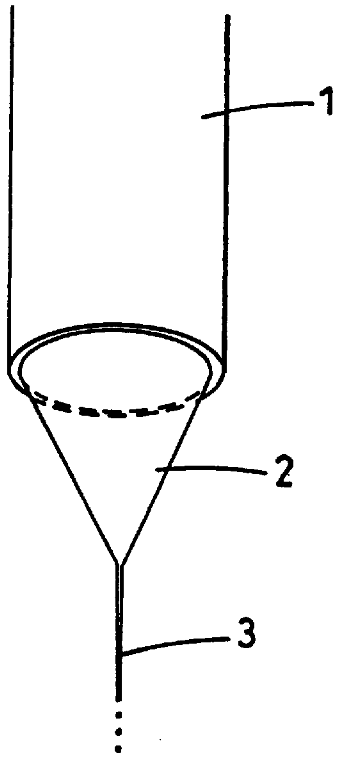
FIGS. 1 to 4 illustrate examples of comminution sites of the device of the invention.

FIG. 1 shows a thin-walled capillary tube (1), which may be of conducting or semiconducting material and which may be electrically connected to a source of high-voltage direct-current, either directly or through the liquid. A single jet (3) is produced from a cusp (2) of liquid, both of which form naturally, according to the voltage and flow rate for a given liquid.

Figure 2:
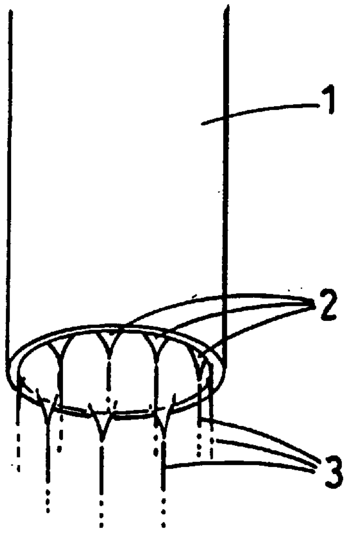

FIG. 2 shows a similar tube (1) used at a lower flow rate and voltage which are adjusted so as to produce multiple cusps (2) and jets (3) issuing from the region of the ends of the thin-walled tube (1).

Figure 3:
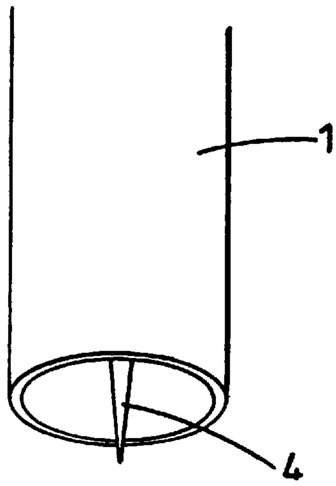

FIG. 3 shows a conducting or semiconducting cylinder (1) which may have a larger diameter than those shown in FIGS. 1 and 2. This nozzle has an inner-member, (4) which is approximately coaxial with the outer tube, (1).

Figure 4:
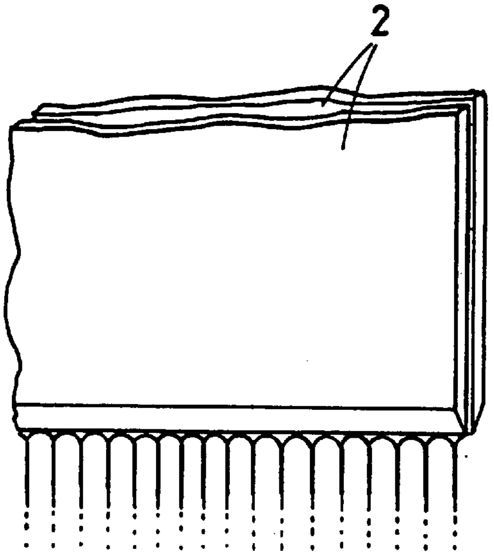

FIG. 4 shows a slot nozzle, formed between two parallel plates (2) having conducting, or semiconducting edges electrically connected to a high-voltage direct-current supply, from which the liquid emerges, forming cusps and jets when the voltage supply and liquid flow rates are suitably adjusted according to the type of liquid being sprayed. For a given jet (and thus droplet) size, and a given liquid, this nozzle may enable a higher flow rate to be achieved than those in which a single cusp and jet are used.

Figure 5:
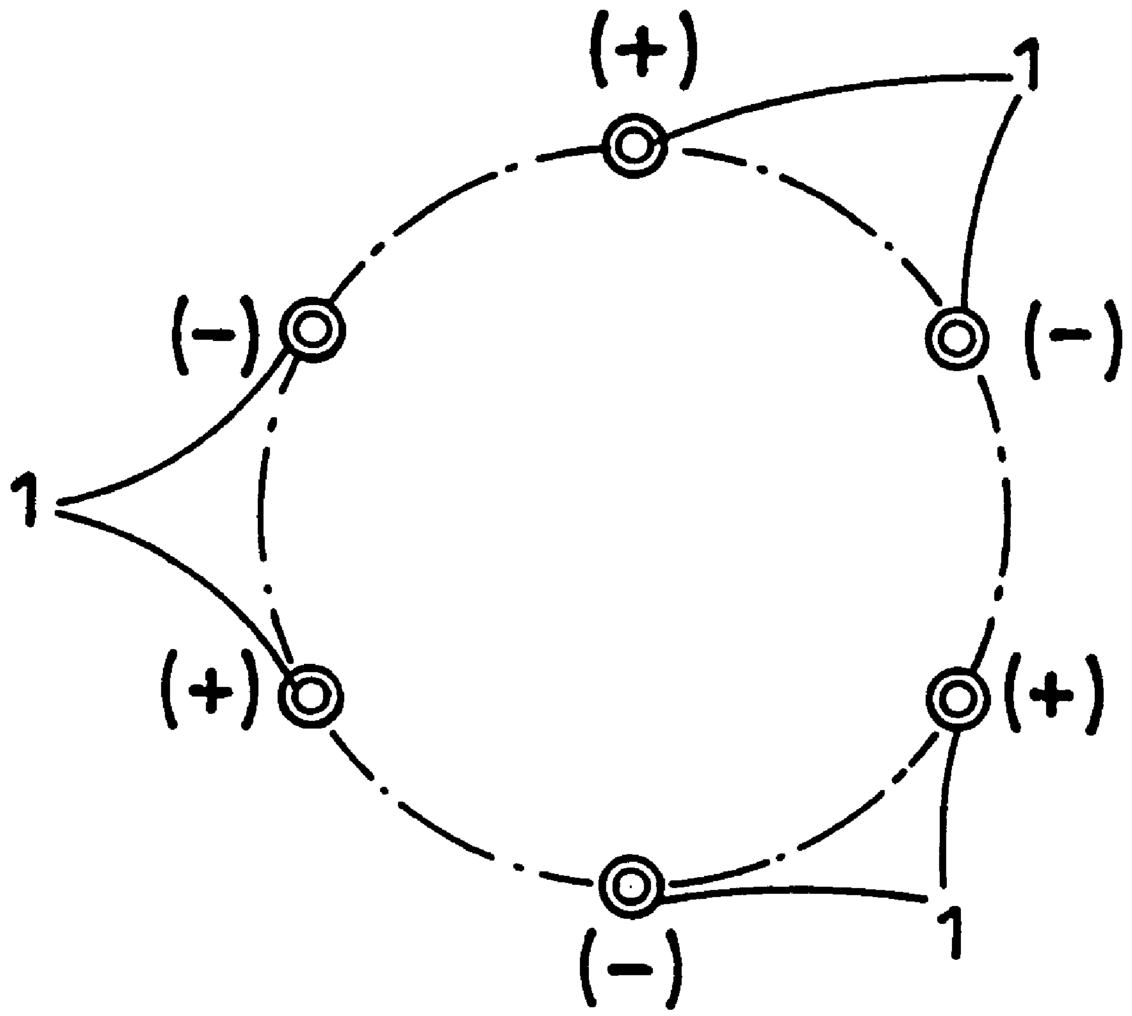
FIG. 5 is a plan view illustrating a multi-nozzle comminution site of the device of the invention.

FIG. 5, shows one example of an array of six nozzles (1) in a circular pattern, centrally mixing the sprays.

Electrical Charging Means

Figure 6:
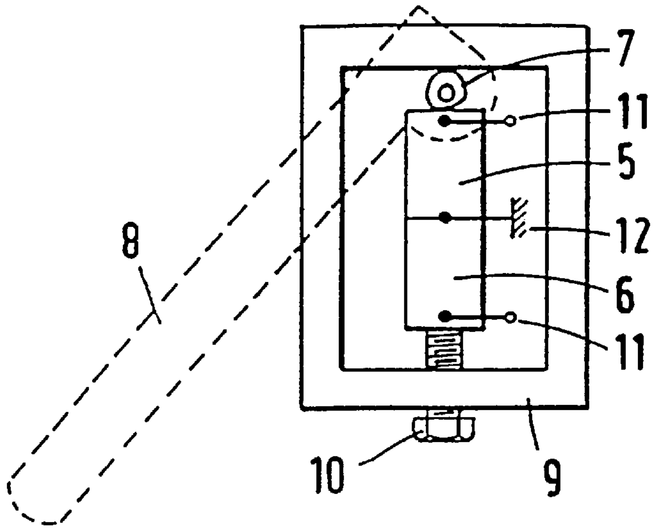
FIG. 6 is a schematic drawing illustrating an example of a charging means of the device of the invention.

An example of this is a piezo electric generator. FIG. 6 illustrates a pair of piezoelectric ceramic generators (5) (6) which may be easily squeezed by a cam (7) operated by a trigger-shaped lever (8). The entire assembly may be housed in a strong steel frame, (9), and the piezoelectric pair may be held tight by adjustment screw (10). The voltage terminals (11) are the two live electrodes for connection to the pumps and nozzles, whilst terminal (12) is earthed, say to the steel frame.

When the lever (8) is pulled inward, the two ceramic generators (5) and (6) will produce high voltages upon the terminals (11) placed at the end surfaces, which may be used to activate both the electrokinetic pumps and the nozzles.

Typical values of charge from say a barium titanate ceramic of about 1.0 cm length and 1.0 sq cm surface area would be 1.0 or 2.0 microcoulomb per squeeze, of either positive or negative polarity. Upon release of the squeezing pressure, a similar charge will flow in the opposite direction. A typical voltage would be say 5,000 to 10,000 volts. Thus, pumping and atomizing may both be achieved by hand operation of a single pair of piezoelectric generators at appropriate voltages, say 5,000 volts, and sufficient currents, say 2.0 microcoulombs per second (2.0 microamperes).

The piezoelectric material may be chosen from several types, such as barium titanate ceramic, or pvdf polymers, which generate significant high-voltage electric charge displacement upon being pressurized. The choice and capacity may be so chosen as to offer control of the degree of pumping and/or atomization when operated. The liquid flow induction, and the nozzle atomization will occur when the piezo-electric generators are squeezed, and again (with opposite polarity) when the piezo-electric generators are released from pressure. The device is arranged so that when squeezed, and when released, the pumps and nozzles will operate without alteration of flow rate or droplet size. Only polarity will change (reverse) in the two modes of operation arising from pressure and release of pressure. This will maintain constant flow and droplet generation, and mixing of species and/or charge-to-mass ratio adjustment of the sprays, during the active modes of pressure, and release of pressure.

Figure 7:
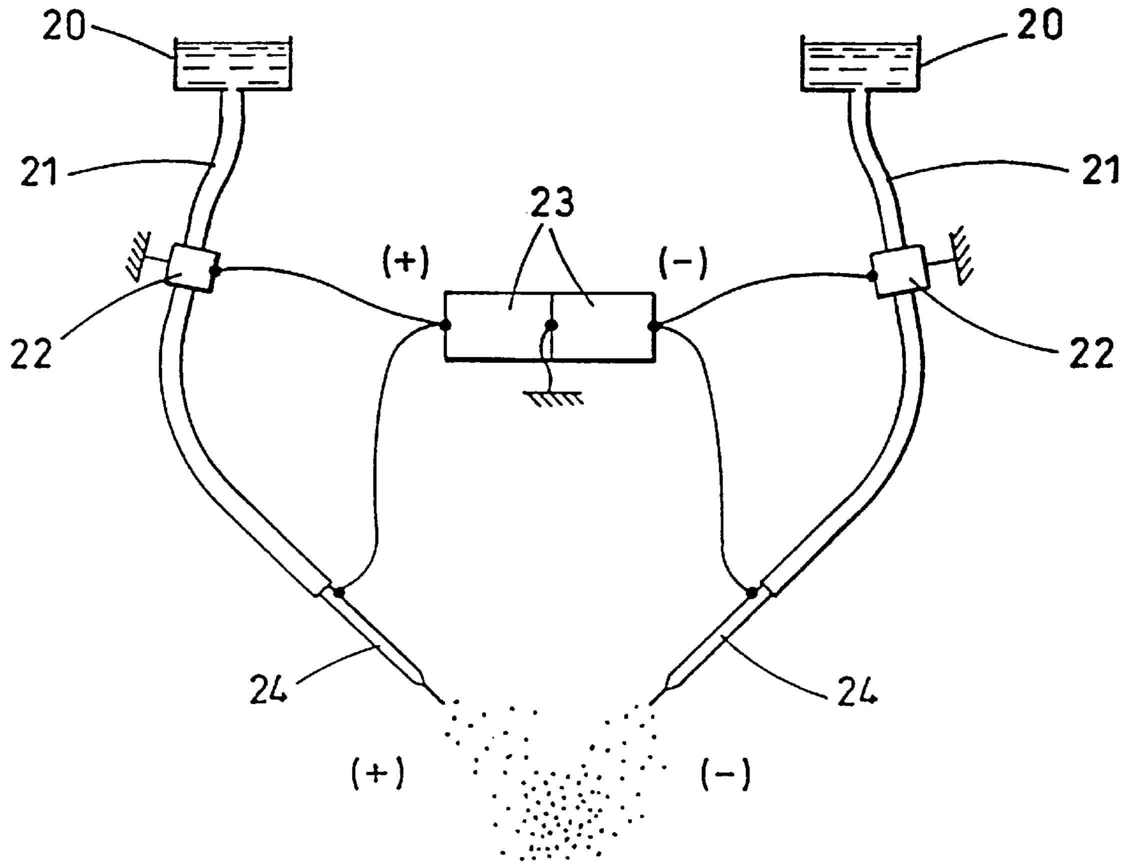
FIGS. 7 and 7*a* are schematic drawings each illustrating an example of a device of the invention.
Figure 7A:
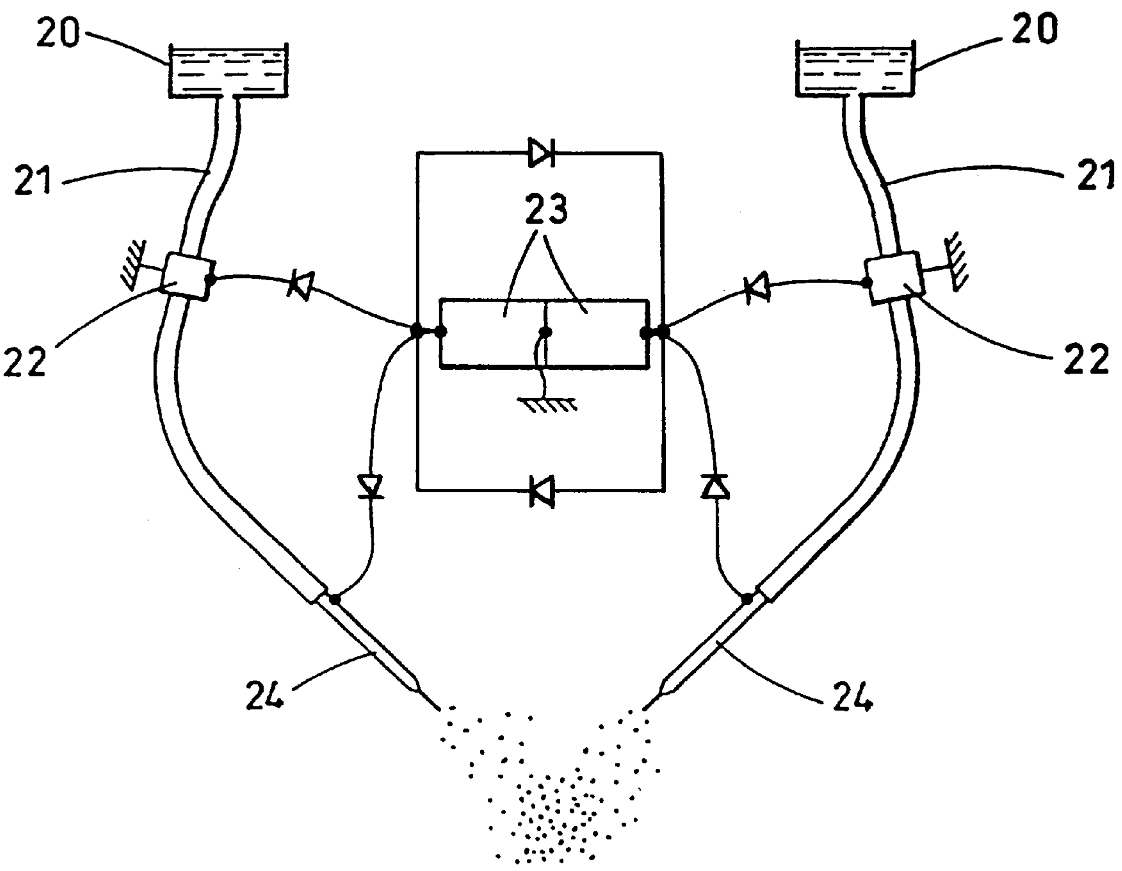

Some forms of electrical pump are sensitive to polarity so that, when using a piezoelectric source of high voltage such as shown in FIG. 7, it would be necessary to form a one-way current flow system, say by using simple diode rectifiers as shown in FIG. 7*a*. FIG. 7*a* also shows how the nozzle polarities may be kept constant if required, by similarly inserting diodes in and between the connecting lines. Thus FIG. 7*a* shows a means of wiring the pumps and nozzles to a pair of piezoelectric generators so that the polarities of the pumps and nozzles remain constant throughout the squeeze and release cycles of the generators.

A schematic representation of the dispenser of the invention is also illustrated in FIG. 7 which shows a dispenser of the invention, in which liquid in each of two reservoirs (20) is caused to flow along suitable conduit, say polyethelene tubing (21) into two electrokinetic pumps (22), say by gravity feed. The two piezoelectric generators (23) are then squeezed so that a high voltage charge is induced at the two faces of the piezoelectric materials. These high voltages will then appear at the terminals of the pumps (22), which are electrically connected to the piezoelectric material by wire conductors.

At the same time, these high voltages will appear at the two conducting, or semi-conducting, capillary-tube nozzles (24). Thus, when the two liquids reach the two nozzles, the liquids will emerge from the nozzles as comminuted droplets with electrical charges of opposing polarity. The droplets will then be attracted to each other by electric field forces, and will tend to mix vigorously to give a charged droplet spray for dispensation to the upper respiratory tract.

The value of droplet charge on each of the two streams of droplets may be independently adjusted to produce the optimum residual value for targeting the upper respiratory tract by one or more of several means: the size, shape, and/or materials of the two piezoelectric materials may be set to give differing values of voltage and charge; the two liquid flow rates may also be adjusted, either by suitable design of the two electrokinetic pumps, or by differing values of piezoelectric voltage applied to the two pumps thus directly influencing droplet charge for a given voltage and nozzle design; and the droplet size and charge of the two liquids may be independently adjusted by the formulations of the two liquids, especially by adjustment of the liquid resistivities.

I claim:

1. A device for comminuting liquid, comprising a plurality of electrohydropdynamic comminution means for forming comminutions having opposite polarities and means for admixing said comminutions of opposite polarities to produce a final comminution having a residual charge other than neutral, each of the electrohydropdynamic comminution means comprising:

a comminution site;

a polarity-sensitive electrical pump for supplying liquid to the comminution site;

a generator for supplying an electric charge to the polarity-sensitive electrical pump; and a one-way current path connecting the generator and the polarity-sensitive electrical pump.

2. A device according to claim 1, comprising an even number of electrohydrodynamic comminution means.

3. A device according to claim 1, wherein said generator is a piezoelectric generator.

4. A device according to either claim 1 or claim 3, wherein the plurality of electrohydrodynamic comminution means are arranged to form comminutions such that the residual charge on the final comminution is fixed.

5. A device according to claim 1 or claim 3, wherein the one-way current path connecting the generator and the polarity-sensitive electrical pump is formed using diode rectifiers.

6. A device according to claim 1 or claim 3, further comprising diodes connected in parallel with the generator to maintain the voltage across the generator at a constant level.

7. A device according to claim 1 or claim 3, further comprising a second one-way current path connecting the generator and the comminution site.

8. A device according to claim 3, wherein the piezoelectric generator comprises a piezoelectric material selected from the group containing berium titanate ceramic and PVDF polymers.

9. A device according to claim 1 or claim 3, when the electrohydrodynamic comminution means are adapted to produce droplets having a diameter in the range of 10 to 25 microns.

10. A device for dispensing a comminution to the upper respiratory tract, comprising a liquid having medicinal qualities for the treatment of disorders of the nasal mucosa, a plurality of electrohydropdynamic comminution means for forming comminutions of the said liquid having opposite polarities and means for admixing the said comminutions of opposition polarities to produce a final comminution having a residual charge other than neutral, each of the electrohydrodynamic comminution means comprising:

a comminution site;

a polarity-sensitive electrical pump for supplying the said liquid to the comminution site;

a generator for supplying an electric charge to the polarity-sensitive electrical pump; and a one-way current path connecting the generator and the polarity-sensitive electrical pump.

11. A device according to claim 10, wherein the liquid is a nasal decongestant.

12. A device according to claim 11, wherein the nasal decongestant is selected from the group containing oxymetazoline, xylometazoline, phenylephrine, propylhexadrine, nephazoline and tetrahydrozoline and as appropriate salts thereof.

13. A device according to claim 10, wherein the said generator is a piezoelectric generator.

* * * * *